United States Patent [19]
Tihon

[11] Patent Number: 5,895,349
[45] Date of Patent: Apr. 20, 1999

[54] FEMALE INCONTINENCE DEVICE

[75] Inventor: Claude Tihon, Eden Prairie, Minn.

[73] Assignee: ContiMed, Inc., Eden Prairie, Minn.

[21] Appl. No.: 08/990,268

[22] Filed: Dec. 15, 1997

[51] Int. Cl.⁶ .................................................. A61F 5/44
[52] U.S. Cl. ........................... 600/29; 128/DIG. 25; 128/885
[58] Field of Search .......................... 128/830–841, 128/885–887; 600/29–32, 574, 582; 602/41, 48, 57

[56] References Cited

U.S. PATENT DOCUMENTS

| | | |
|---|---|---|
| 4,421,511 | 12/1983 | Steer et al. . |
| 4,496,355 | 1/1985 | Hall et al. . |
| 4,795,449 | 1/1989 | Schneider et al. . |
| 4,822,347 | 4/1989 | MacDougall . |
| 4,846,819 | 7/1989 | Welch . |
| 4,938,218 | 7/1990 | Goodman et al. ................ 600/338 |
| 5,059,189 | 10/1991 | Cilento et al. ................... 604/48 X |
| 5,717,005 | 2/1998 | Richardson ..................... 602/48 X |

FOREIGN PATENT DOCUMENTS

| | | | |
|---|---|---|---|
| 2193438 | 2/1988 | United Kingdom ............... 600/29 |
| 96/39989 | 12/1996 | WIPO ............................... 600/29 |

Primary Examiner—Samuel Gilbert
Attorney, Agent, or Firm—Nikolai, Mersereau & Dietz, P.A.

[57] ABSTRACT

A device for managing urinary incontinence in a human female comprises a soft, non-porous dome-shaped suction cup like device having a flat annular zone about its periphery and adapted to cooperate with the vestibule floor of female genitalia for blocking the flow of urine without being in physical contact with the urethral meatus.

11 Claims, 2 Drawing Sheets

FEMALE INCONTINENCE DEVICE

BACKGROUND OF THE INVENTION

I. Field of the Invention

This invention relates to devices used to relieve or mitigate the problems associated with human female stress incontinence and more specifically to a removable seal for covering the urethral meatus of a human female subject.

II. Discussion of the Prior Art

A good discussion of problems relating to female urinary incontinence is set forth in the "Background of the Invention" of U.S. Pat. No. 5,336,208 to Rosenbluth et al. That material is incorporated by reference herein.

The Rosenbluth et al. '208 patent describes a urethral meatus occlusion device for managing urinary incontinence in a human female that includes a resilient pad shaped to fit between the labia minora and the floor of the vestibule of the vulva to occlude the urethral meatus. The device is held in place by an adhesive to provide a sealing engagement with the urethral meatus. The pad comprises a highly absorbent, hydrophilic material having a longitudinal ridge with a posterior edge to allow gripping during installation and removal. In accordance with another disclosed embodiment, the pad comprises a flexible sack filled with a liquid or gel that will conform to the female genitalia so as to again occlude the urethral meatus.

The current invention is an improvement over Rosenbluth et al. '208 in that the current invention employs both a minor vacuum from the dome and an adhesive boarder to provide secure attachment of the device to the vestibule floor of the female vulva. Lesser adhesive surface used results in a lesser area of occluded skin surfaces. This permits the vestibule floor skin to breathe better and lessen the possibility of skin ulceration. Furthermore, the current invention offers another improvement over the device described in the Rosenbluth patent in that the urethral meatus will not be occluded by the physical contact of adhesives as in Rosenbluth. This minimizes the possibility of infection by migration of foreign substances directly into the metal opening, as well as physical irritation to the meatus. The minor suction provided by my invention also helps to seal the metal opening and further aid in the continence of the patient and the minimization of upward migration of foreign materials.

SUMMARY OF THE INVENTION

In accordance with the present invention, a device for managing urinary incontinence in a human female comprises a soft, non-porous sheet of elastomeric material having an annular base surrounding a compressible, hollow dome, the base being shaped to conform to and seal against the vestibule floor of the subject's external genitalia with the hollow dome adapted to overlay and be out of contact with the urethral meatus. The compressible dome functions as a suction cup so that when squeezed and released, the device sealingly adheres to the vestibule floor while blocking the flow of urine out the urethral meatus.

In accordance with an alternative embodiment, the annular base may be provided with an adhesive layer to enhance adherence of the device to the vestibule floor. The base is shaped so as to surround the urethral meatus while remaining out of contact with the clitoris and vaginal opening.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
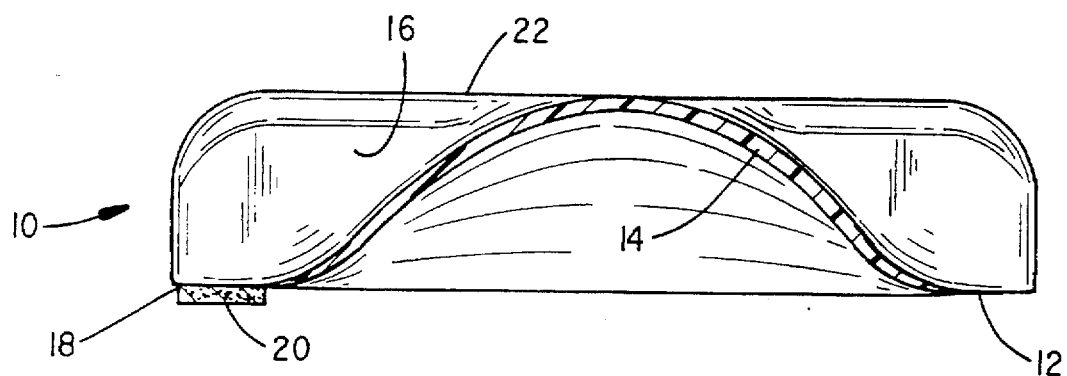
FIG. 1 is a partially sectioned side view of the device taken along line 1—1 in FIG. 2 comprising a preferred embodiment of the present invention.
Figure 2:
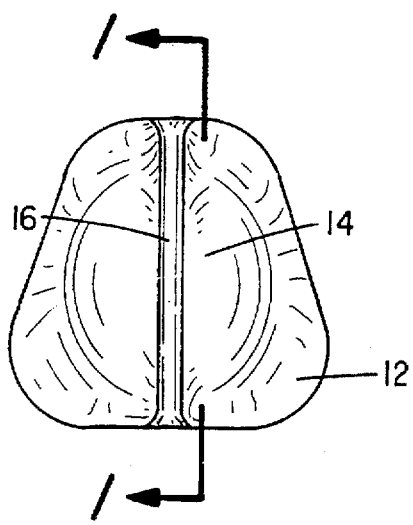
FIG. 2 is a top plan view of the embodiment of FIG. 1.

Referring to FIGS. 1 and 2 of the drawings, the device 10 of the present invention for managing urinary incontinence in human females comprises a soft, non-porous sheet of elastomeric material having a flat annular base portion 12 surrounding a compressible, hollow dome portion 14. The base is shaped to conform to the female genital anatomy. More particularly, the base portion 12 is designed to seal against the vestibule floor of the vulva and with the dome 14 suspended over and out of contact with the urethral meatus.

As shown in FIG. 2, the device is generally trapezoidal in shape in its plan view and when installed, the narrow end will be the anterior, pointing toward the clitoris. The larger end will be posterior, pointing toward but not covering the vaginal opening. The side edges of the device, when properly installed reside between the labia minora.

To assist in inserting and removing the device 10, it is provided with a handle portion 16 in the form of a narrow wing that spans the dome portion 14 and projects outwardly from the annular base portion 12. The device can be readily gripped between the thumb and forefinger and inserted such that the flat base portion seals against the floor of the vestibule. To assist in sealing, a suitable, non-irritating gel may be applied to the undersurface of the annular base portion 12 and then by compressing the dome 14 as the device is moved into position and then releasing the dome, a vacuum is created which assists in securing the device to the vestibular floor. The use of a gel inhibits breaking of the vacuum in the same way that moistening a conventional suction cup provides better adherence to a smooth flat surface. The sheet material is of a greater thickness in the area defining the dome than it is in the annular base region, thus affording an increased memory property and thereby enhancing the suction cup effect.

It is also contemplated that the undersurface of the flat annular base portion may be treated with a pressure sensitive adhesive, as at 18, with the adhesive being protected by a sheet of release paper 20 prior to its use.

As seen in FIG. 1, the handle portion 16 is relatively smooth but preferably has concave side walls resulting in a thicker and radiused upper free edge 22. The wing-like handle 16 permits easy removal of the device by effectively lifting the device from one of its ends, resulting in a pealing action for breaking the minor vacuum seal and comfortable removal thereof.

Because the elastomeric material from which the device is fabricated is both non-absorbent and non-porous, when properly installed, it prevents urine linkage due in part to the minor vacuum created by the suction cup effect as the device is installed which results in closure of the urethral meatus.

Figure 3:
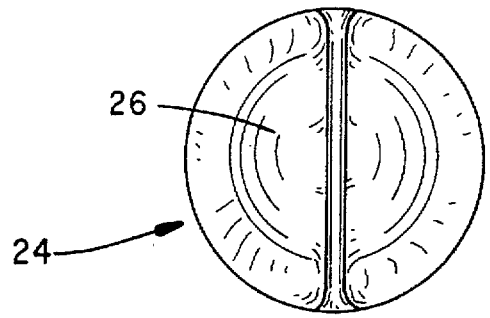
FIG. 3 is a top plan view of an alternative embodiment.

FIG. 3 illustrates an alternative embodiment 24 which is similar in all respects to the embodiment of FIG. 2 except that rather than being trapezoidal in shape, it is circular in shape in its plan view. The diameter of the device of FIG. 3 allows it to be inserted between the labia minora with the dome portion 26 overlying the urethral meatus. In both the embodiment of FIGS. 2 and 3, the elastomeric material is thicker in the dome portion than at its periphery and as indicated earlier it will possess a sufficient memory property to return to its pre-stressed state after having been squeezed and thereby creating a vacuum under the dome portion thereof.

It is possible to reduce the wall thickness of the dome portion of the device by incorporating open-cell foam material within the device to provide the reexpansion following the squeezing and exhaustion of air from the dome and placement of the device on the vestibule floor. Rather than relying upon the memory property of the material comprising the dome to provide the necessary reexpansion, the self-expanding properties of the foam material creates the desired vacuum.

Figure 4:
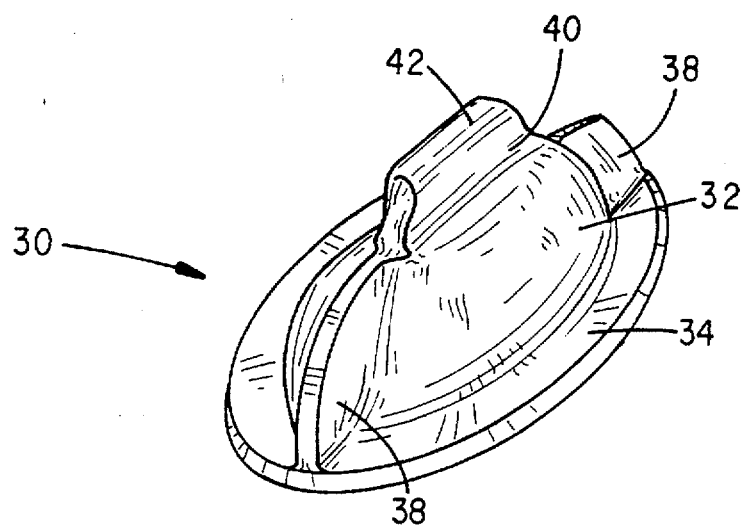
FIG. 4 is a perspective view of a further alternative embodiment.
Figure 5:
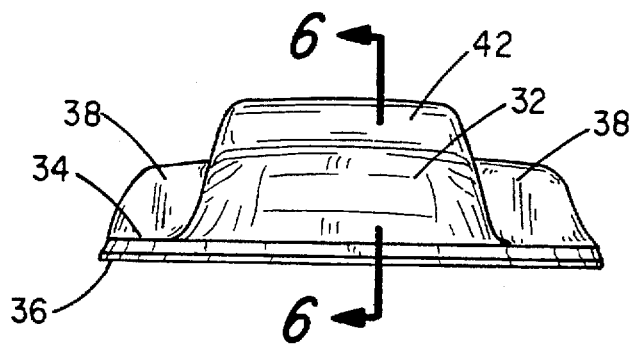
FIG. 5 is a side view of the embodiment of FIG. 4.

Referring to FIG. 4, the device 30 for managing urinary incontinence is seen to comprise a thin walled hollow plastic dome 32 that is preferably molded from a suitable medical grade plastic, such as polyurethane, polyethylene, silicone rubber and the like. The dome 32 is surrounded by an integrally formed annular base portion 34, the undersurface of which may be provided with an adhesive layer 36 to facilitate attachment as with the previously described embodiment.

To facilitate placement and later removal, the device 30 preferably includes outwardly projecting flat wing-like handles 38.

Figure 6:
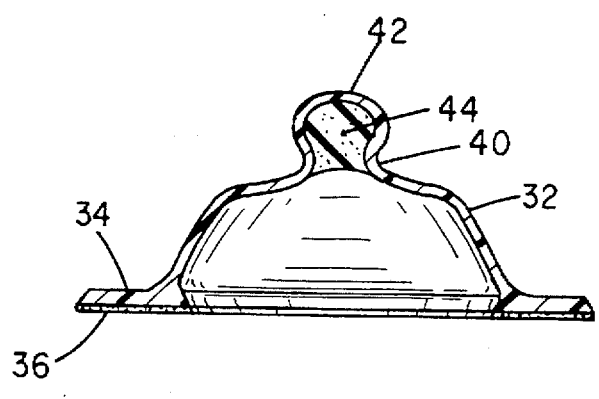
FIG. 6 is a cross-sectional view taken along line 6—6 in FIG. 5.

As can be seen in the perspective view of FIG. 4 and the cross-sectional view of FIG. 6, the dome necks down as at 40 and then enlarges to form a compartment 42 that is filled with an open-cell foam material 44. The interior of the compartment 42 is in fluid communication with the interior of the dome 32.

In use, a female suffering from stress incontinence will remove a release paper layer from the base of the device 30 so as to expose the adhesive layer 36. While squeezing the compartment 42 and thereby compressing the foam 44 to exhaust air therefrom, the base 34 of the device is placed against the floor of the vestibule so that the dome 32 overlays but does not contact the urethral meatus. Once intimate contact has been established between the base 34 and the vestibule floor, the squeezing pressure of the user's fingers on the compartment 42 is released allowing the foam material to self-expand and create a partial vacuum within the dome structure. The neck 40 permits the compartment 42 to fold over against the dome so as not to create a noticeable bulge or to interfere with the user's undergarments.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A device for managing urinary incontinence in a human female having external genitalia that includes a vulva with a vestibule floor, a clitoris, labia minora and having a urethral meatus between the labia minora, comprising:

a soft, impermeable sheet of elastomeric material having a flat, flexible base surrounding a compressible, hollow dome, the dome including a compartment therein, the compartment containing an open-cell, self-expanding foam material therein, the base being shaped to conform to and seal against the vestibule floor with the hollow dome adapted to overlay and remain out of contact with the urethral meatus.

2. The device of claim 1 and further including:

a handle projecting outwardly of the base to facilitate grasping, and placement and removal of the device.

3. The device of either of claims 1 or 2 wherein a portion of the sheet comprising the compressible hollow dome and compartment is sufficiently compliant such that when the dome and compartment is deformed by being squeezed, the self-expanding foam seeks to return to an uncompressed condition when released, creating a partial vacuum within the hollow dome.

4. The device of claim 3 wherein a portion of the sheet comprising the base of a lesser thickness than the portion of the sheet comprising the hollow dome.

5. The device of claim 3 wherein the vacuum within the hollow dome serves to close off the urethral meatus when the base is sealed against the vestibule floor of the vulva.

6. The device of claim 1 wherein the base is shaped to avoid contact with the meatus, clitoris and vaginal opening when the base is positioned on the vestibule floor.

7. The device of claim 6 wherein the base is generally trapezoidal.

8. The device of claim 1 and further including a non-irritating, body-compatible, pressure-sensitive adhesive on a surface of the base and adapted to aid in the device to the vestibule floor.

9. The device of claim 8 and further including a medicament distributed throughout the adhesive.

10. The device of claim 8 and further including a removable release paper covering the adhesive prior to application of the device to the vestibule floor.

11. The device of any one of claims 1, 2, 8, 9, or 10 wherein the portion of the sheet surrounding the hollow dome is of a lesser thickness than the portion of the sheet comprising the hollow dome.

* * * * *

UNITED STATES PATENT AND TRADEMARK OFFICE
CERTIFICATE OF CORRECTION

PATENT NO. : 5,895,349
DATED : April 20, 1999
INVENTOR(S) : Claude Tihon

It is certified that error appears in the above-indentified patent and that said Letters Patent is hereby corrected as shown below:

Column 4, line 44 (claim 8), after "adhesive" insert -- disposed --. Line 45, after "in" insert -- sealing --.

Signed and Sealed this

Fifth Day of October, 1999

*Attest:*

Q. TODD DICKINSON

*Attesting Officer*  *Acting Commissioner of Patents and Trademarks*